US 6,700,666 B2

(12) United States Patent
Blouin et al.

(10) Patent No.: US 6,700,666 B2
(45) Date of Patent: Mar. 2, 2004

(54) ULTRASONIC VIBRATION DETECTION USING FREQUENCY MATCHING

(75) Inventors: Alain Blouin, Montreal (CA); Denis Drolet, Montreal (CA); Jean-Pierre Monchalin, Montreal (CA); Christian Padioleau, Montreal (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 10/128,339

(22) Filed: Apr. 24, 2002

(65) Prior Publication Data

US 2002/0167676 A1 Nov. 14, 2002

Related U.S. Application Data (60) Provisional application No. 60/285,692, filed on Apr. 24, 2001.

(51) Int. Cl.$^7$ .................................................. G01B 9/02
(52) U.S. Cl. ........................................................ 356/502
(58) Field of Search ............................. 356/28.5, 432, 356/477, 498, 502

(56) References Cited

U.S. PATENT DOCUMENTS

| | | | |
|---|---|---|---|
| 4,180,328 A | 12/1979 | Drain | 356/349 |
| 4,822,164 A | 4/1989 | Breen | 356/28.5 |
| 5,070,483 A | 12/1991 | Berni | 367/14 |
| 5,481,356 A | * 1/1996 | Pouet et al. | 356/35.5 |
| 5,680,212 A | 10/1997 | Blouin et al. | 356/357 |
| 6,078,397 A | 6/2000 | Monchalin et al. | 356/357 |
| 6,115,123 A | 9/2000 | Stappaerts et al. | 356/345 |

* cited by examiner

*Primary Examiner*—Samuel A. Turner
*Assistant Examiner*—Michael A. Lyons
(74) *Attorney, Agent, or Firm*—Marks & Clerk (57) ABSTRACT

In order to probe an object in motion subject to surface displacement, for example, caused by ultrasonic wave propagation, a laser beam is split into a first portion and a second portion. The first is scatted off the object to generate a signal beam. The frequency shift produced in the signal beam due to motion of the object is measured, and this is used to adjust the frequency of one or both portions of the laser beam so that both beams have substantially the same frequency. The surface displacements are measured by comparing the second portion of the laser beam and the signal beam after frequency adjustment.

33 Claims, 6 Drawing Sheets

ULTRASONIC VIBRATION DETECTION USING FREQUENCY MATCHING

This application claims the benefit of U.S. Provisional Application Ser. No. 60/285,692 filed Apr. 24, 2001.

BACKGROUND OF THE INVENTION

1. Field of the Invention

This invention relates to the field of materials analysis, and in particular to a method and apparatus for probing an object in motion with the aid of small surface displacements generated, for example, by ultrasonic energy.

2. Description of Related Art

Two-beam adaptive phase demodulators are used for noncontact and non-invasive measurements of the small surface displacements produced by ultrasonic waves propagating in an object. These devices are based on the illumination of the surface of the object by a probing laser, collection of the light scattered by the surface of the object and its mixing with a beam directly derived from the laser (the pump beam). They are adaptive in the sense they can operate with light scattered by rough surfaces and having speckles and in the presence of various ambient perturbations. The ultrasonic waves to be detected are often generated by a pulsed laser. The combination of generation and detection in a technique called laser-ultrasonics is recognized to be a powerful and versatile technique for inspecting objects and industrial products. When the object is in rapid motion along the line-of-sight of the probing laser or when the laser beam is rapidly scanned, these two-beam adaptive phase demodulators become very insensitive and in practice useless. This invention provides a practical solution to this problem and allows the two-beam adaptive phase demodulators to be used even in the case of rapid motion of either the object or the probing laser beam.

Laser-ultrasonics is a powerful nondestructive evaluation technique based on the generation and the detection of ultrasound with lasers. A short pulse high power laser is used for generating the ultrasonic waves using either a thermoelastic mechanism (noninvasive) or material ablation. The detection of the ultrasonic waves is performed with a second laser coupled to an optical demodulator which measures the phase modulation of the laser light scattered or reflected by the surface. This phase modulation is induced by the small ultrasonic displacement of this surface. Several solutions have been developed to detect and demodulate efficiently the scattered light in the practical cases of industrial interest where the surface is rough and the scattered light has speckles.

A first type of solution is based on time-delay interferometers that have been field-widened. J. -P. Monchalin, *Optical Detection of Ultrasound*, IEEE Trans. Sonics, Ultrasonics, Freq. Control, UFFC-33, p. 485–499 (1986). Particularly useful and practical are the various confocal Fabry-Perot schemes described in several US patents, for example, J. -P. Monchalin, Optical Interferometric Reception of Ultrasonic Energy, U.S. Pat. No. 4,659,224; J. -P. Monchalin, Broadband Optical Detection of Transient Surface Motion From a Scattering Surface, U.S. Pat. No. 4,966,459; and R. Heon and J. -P. Monchalin, Optical detection of a surface motion of an object using a stabilized interferometric cavity, U.S. Pat. No. 5,137,361. Such a demodulator has a rather short response time to a change of phase or frequency of the collected scattered light (across the whole field or change of the distribution): values of 100 ns or shorter are typical and depend upon the cavity length and mirrors reflectivity. Therefore such systems easily tolerate strong vibrations and motions of the probed object. Such motions cause not only a change of the speckle pattern but also, if they have a component along the line-of-sight a change of frequency (Doppler effect). Finally it should be noted that, for proper operation of the Fabry-Perot based devices, the laser frequency should be locked to the cavity length, which requires a laser with an adjustable frequency or an adjustable cavity length and locking electronics.

A second solution consists in the various two-beam adaptive phase demodulator schemes, in which the beam scattered by the surface is mixed with a beam directly derived from the laser (the pump beam) in a sensing material. This sensing material has trapping sites for the charges produced by the photoelectric effect. After charge motion by diffusion or drift (if an electric field has been applied) and trapping, a charge distribution is set in the material and results in an electric field distribution (the space-charge field distribution). Three different schemes based on this approach are known. First, two-wave mixing (TWM) in a photorefractive crystal operated in the diffusion regime, i.e. without any voltage applied to the crystal, was proposed by Monchalin: J. -P. Monchalin, R. K. Ing, Broadband Optical Detection of Transient Motion From a Scattering Surface by Two-Wave Mixing in a Photorefractive Crystal, U.S. Pat. No. 5,131,748; R. K. Ing and J. -P. Monchalin, *Broadband Optical Detection of Ultrasound by Two-Wave Mixing in a Photorefractive Crystal*, Appl.Phys.Lett. vol. 59, pp.3233–3235, 1991; and A. Blouin, J. -P. Monchalin, *Detection of ultrasonic motion of a scattering surface by two-wave mixing in a photorefractive GaAs crystal*, Appl. Phys. Lett. 65, 932, (1994). For the TWM setup, the signal beam at the output of the crystal is composed of the signal beam transmitted through the crystal and of the beam from the pump beam diffracted by the grating, which is wavefront adapted to the signal beam. This signal beam at the output of the crystal is then sent to an optical detector or to a balanced receiver. This TWM-based ultrasonic demodulator was later extended to a crystal under a transient applied voltage. A. Blouin, P. Delaye, D. Drolet, J. -P. Monchalin and G. Roosen, Sensitive and Fast Response Optical Detection of Transient Motion From a Scattering Surface by Two-Wave Mixing, U.S. Pat. No. 5,680,212. P. Delaye, A. Blouin, D. Drolet, L. A. de Montmorillon, G. Roosen, J. -P. Monchalin, *Detection of ultrasonic motion of a scattering surface by photorefractive InP:Fe under an applied field*, Journal of the Optical Society of America, B 14, 1723, (1997). Instead of a photorefractive crystal, the TWM device can also be operated with a photorefractive polymer material (Klein, M. B., Bacher, G. D., Grunnet-Jepsen, A., Wright, D., Moerner, W. E., *Homodyne detection of ultrasonic surface displacements using two-wave mixing in photorefractive polymers*, Optics-Communications. vol.162, no.1–3; Apr. 1, 1999; p.79–84), photorefractive quantum wells or with other non-linear materials. A sketch of the TWM optical demodulator scheme is shown in FIG. 1.

Figure 1:
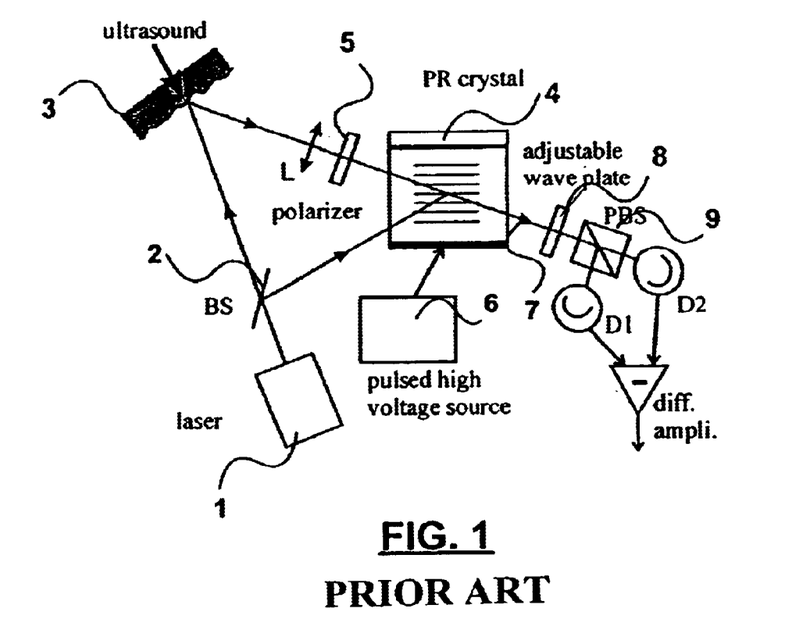
FIG. 1 is a schematic diagram of a prior art TWM optical demodulator for the measurement of ultrasonic waves on a rough surface.

In FIG. 1, laser 1 outputs a beam that is passed through a beam splitter 2. A portion of the output beam is directed at the sample 3, which is excited with ultrasonic energy, and a second portion is directed at the photorefractive crystal 4, where it is combined with the beam scattered off the sample 3 after passing through a lens L and polarizer 5.

The photorefractive crystal is energized with a pulse high voltage source 6 and outputs a beam 7 that passes through adjustable quarter wave plate 8 and polarizing beam splitter 9. The polarized output beams are received by photodetectors D1 and D2 and passed to the respective inputs of differential amplifier.

A second scheme based on the photo-electromotive force (p-EMF) was proposed by Petrov. M. P. Petrov, I. A. Sokolov, S. I. Stepanov, G. S. Trofimov, 'Non-steady-state photo-electromotive-force induced by dynamic gratings in partially compensated photoconductors', J. Appl. Phys. 68, 2216, (1990). The p-EMF-based device does not requires the crystal to have electro-optic properties, which means that the written space-charge field does not necessarily produces a refractive index grating. A third scheme, proposed more recently is based on the self-polarization modulation effect. K. Paivasaari, A. A. Kamshilin, *Adaptive sensors of rough-surface ultrasonic vibrations based on the polarisation self-modulation effect*, Fourth International Conference on Vibration Measurements by Laser Techniques: Advances and Applications, SPIE Proceedings vol. 4072, 70, (2000).

Two-beam adaptive demodulators make much more compact devices than the confocal Fabry-Perot based systems. They have also a broader frequency response bandwidth, extending to low ultrasonic frequencies and without drop-off gaps at high frequencies. They also. do not require any active stabilization. For these reasons they appear much more promising than the confocal Fabry-Perot based systems. To operate in the presence of strong vibrations or on moving objects, efforts have been directed to shortening the response time of these two-beam adaptive phase demodulators. A short response time is either obtained by design (e.g. small angle between the interfering beams) and/or by strong pumping. In spite of these efforts it is difficult to get a response time as short as the confocal Fabry-Perot. Therefore two-beam adaptive phase demodulators, although very attractive from several aspects, have serious shortcomings when the object is in motion. Particularly troublesome is the case where the motion is not transverse to the line-of-sight, so the change produced by the motion is not only a change of the speckle pattern but also a change of the optical frequency of the light scattered (Doppler effect).

Figure 2:
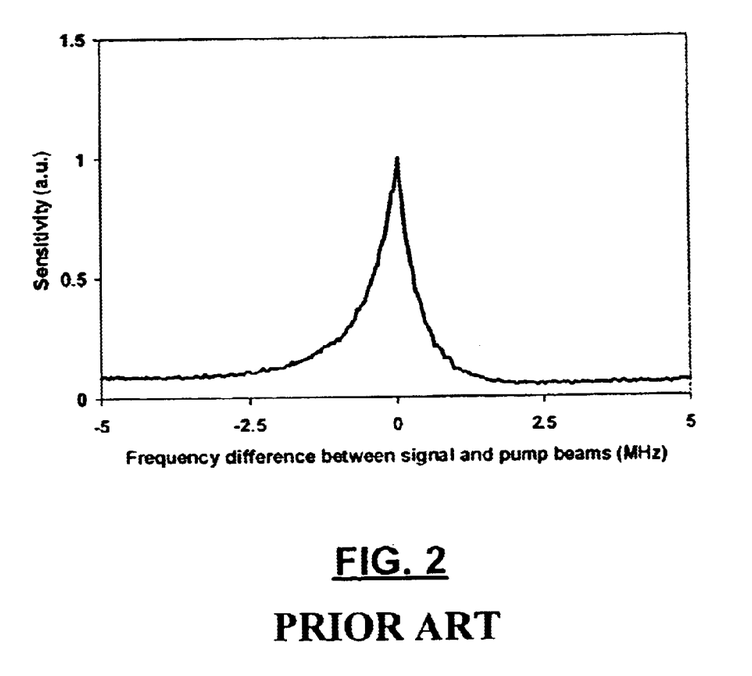
FIG. 2 shows the sensitivity of the TWM-based phase demodulator operated with a GaAs crystal in the diffusion regime versus the optical frequency difference between the signal and pump beams. An electro-optic phase modulator was harmonically driven at 10 MHz to simulate the surface displacement. The response time of the crystal was about 0.7 μs.

In the three two-beam adaptive phase demodulator schemes, a difference between the optical frequencies of the pump and signal beams makes the interference pattern produced by these two beams moving. Since the buildup time of the space charge is finite, the space charge cannot exactly follow the moving interference pattern. The space-charge field amplitude is then reduced and eventually, for a large enough frequency difference the space-charge field is washout. This reduction of the space-charge field amplitude decreases the sensitivity of the device to the phase modulation induced by the small surface displacements. As an example, the sensitivity of the TWM-based device operated with a GaAs crystal in the diffusion regime versus the optical frequency difference between the signal and pump beams is shown in FIG. 2. In this experiment, the laser was a Nd:YAG laser at 1.064 $\mu$m wavelength, the signal beam was phase modulated using an electro-optic phase modulator driven at 10 MHz and the optical frequency difference between the pump and signal was produced by an acousto-optic shifter on the pump beam. In the diffusion regime, the sensitivity is reduced by a factor of approximately 2 for $\Delta\nu\tau\approx\frac{1}{2}\pi$, where $\Delta\nu$ is the optical frequency difference between the signal and pump beams and $\tau$ is the grating buildup time. In this experiment, $\tau$ was about 0.7 $\mu$s and the sensitivity is reduced by a factor 2 for an optical frequency difference of about 0.2 MHz. In the drift regime, the sensitivity reduction is not symmetric over positive or negative frequency differences since the high voltage applied to the crystal gives a preferential drift direction of the charges.

A Doppler optical frequency difference between the pump and signal beam optical frequencies is obtained when collecting the laser light scattered off an object in motion along the line-of-sight of the laser or in motion along the collection direction. Alternatively, a Doppler frequency shift of the scattered light is also obtained when the scanning laser beam does not impinge normally to the surface of the object, for example when scanning a contoured object. When the incident laser beam and the collection direction are collinear, the frequency shift of the scattered beam is simply proportional to the component along the line-of-sight of the velocity of laser spot on the object. As an example, with a laser wavelength of 1.064 $\mu$m, the 0.2 MHz half-reduced sensitivity of FIG. 2 corresponds to an object velocity of 0.1 m/s along the line-of-sight of the laser. There are many practical situations where velocity higher than 0.1 m/s are encountered making the two-beam adaptive demodulator-based systems insensitive and useless. For example, in the application to the measurement of an oil slick thickness from an airplane, such frequency shifts higher than 0.1 m/s are readily encountered and are caused by the vertical motion of the airplane. M. Choquet, R. Héon, G. Vaudreuil, J. -P. Monchalin, C. Padioleau, R. H. Goodman, *Remote thickness measurement of oil slicks on water by laser-ultrasonics* Proceedings of the 1993 International Oil Spill Conference, pp. 531, (1993).

Such a frequency shift may also be found when inspecting objects submitted to large amplitude vibrations at low frequencies or materials like a paper web or a metal sheet in rapid motion on a production line. For example, the in-plane Young's modulus of a paper web is deduced from the on-line measurement of ultrasonic in-plane surface displacement. This in-plane displacement measurement requires that the laser impinges at oblique incidence on the paper web, which results in a frequency shifted light collected back from the paper web. In a recent patent by Brodeur (P. H. Brodeur and E. F. Lafond, Non-contact measurements of ultrasonic waves on paper webs using a photorefractive interferometer, U.S. Pat. No. 6,115,12714), it is claimed that a TWM photorefractive demodulator can be used for on-line paper web measurements but this approach does not work in practice because the velocity component along the line-of-sight is of the order of 10 m/s (when detecting in-plane waves with a beam oriented at about 45° with respect to the web in the machine direction). It is nearly impossible to have a TWM system, even by using semiconductor photorefractive crystal with strong pumping that could tolerate the corresponding very large frequency offset. A sufficiently fast system may be eventually obtained with the p-EMF-based scheme since in this case the angle between the beams that give the optimum sensitivity is smaller. Furthermore, even if the system is made very fast response, it cuts strongly low frequencies (below 1 MHz) that are needed for this application. Another important example is the inspection of polymer-matrix composite objects used in the aerospace industry. Laser ultrasonics is noteworthy for the ease of inspecting complex geometries and the technology has actually been commercialized by using a confocal Fabry-Perot as demodulator. The use of photorefractive-based systems would be of interest for their sensitivity at low frequencies and for inspecting thick objects, but it should be realized that this application requires fast scanning (one meter per second and more). In the case of contoured objects, since there is oblique incidence of the probing laser beam (of 45° and more), very large frequency shifts then result, making any two-beam adaptive phase demodulator insensitive.

SUMMARY OF THE INVENTION

According to the present invention there is provided a method of probing an object in motion, comprising generating a laser beam and splitting said laser beam into a first portion and a second portion; directing said first portion of said laser beam at said object to generate a signal beam scattered from a surface thereof; determining the frequency shift produced in the signal beam due to motion of the object; adjusting the frequency of one or both of said first and second portions of said laser beam so that both said second portion of said laser beam and said signal beam have substantially the same frequency; and measuring displacements of said surface by comparing said second portion of said laser beam and said signal beam after said frequency adjustment.

Typically, the surface displacements are caused by ultrasonic waves propagating through the object.

The motion of the object causes modification of the speckle pattern to which the space-charge field should also adapt. The inventors have found that this effect is tolerable and with adequate configuration and sufficient pumping level, the space-charge field adapts itself sufficiently rapidly so there is no significant loss of sensitivity. The present invention overcomes the large frequency offset linked to the fast motion of either the object or the inspection beam while maintaining the sensitivity to low frequency ultrasound.

To circumvent the Doppler frequency shift produced by the velocity of the inspected object or of the laser spot on the object, the invention thus employs a dynamic compensation scheme. The approach is based on two steps: first the velocity or the frequency shift is evaluated, second, the frequency of one of the interfering beams (preferably the pump beam) is shifted in such a way that both beams are substantially at the same frequency. The velocity can be measured by a number of ways depending upon the application. For example, in the application of the slick oil thickness measurement the airplane vertical velocity can be obtained from an accelerometer whose output is integrated to get the velocity. In the application to the measurement of the elastic parameters and the tension of a paper web, the velocity of the web is known through encoders mounted on the shaft of rollers or others standard sensors used in the paper industry.

In some case optical velocimeters can be used. These can be based on differential anenometry and several commercial versions are available. A system based on two-beam interferometry, which is essentially a Michelson interferometer, can also be used. The amplitude of the signal is highly variable, because of speckle, but includes a beat note proportional to the velocity along the line-of-sight of the probe. Velocimeters based on photorefractive crystals could also be used and two approaches have been described. See, P. Delaye, S. de-Rossi, G. Roosen, *Photorefractive vibrometer for the detection of high-amplitude vibrations on rough surfaces*, J. of Opt. A, 2, 209, (2000); and C. C. Wang, F. Davidson, S, Trivedi, *Simple laser velocimeter that uses photoconductive semiconductors to measure optical frequency differences*, Appl. Opt. 34, 6496, (1995), the contents of which are herein incorporated by reference.

Another velocimeter scheme based on imparting on the probe beam frequency chirped optical sidebands may also be used. See. Blouin, C. Padioleau, D. Drolet, *Photorefractive adaptive wavefront velocimeter based on chirped phase modulation*, Program of the 1999 Quantitative NonDestructive Evaluation Conference, pp.120, (1999), the contents of which are herein incorporated by reference.

For a contoured object scanned by the laser, the velocity of the object with respect to the laser spot can be determined by using a range finder at the same time as scanning. If the beam of the range finder is scanned colinearly with the probing beam, the change of distance for a given time interval gives directly the velocity along the line-of-sight. Various principles can be used to measure distance, such as for example laser triangulation and high frequency intensity modulation of the ranging beam. This last technique is based on the determination of the time delay of the modulation observed in the scattered light from the surface. It also possible to perform this range determination (from which the shape of the object can in particular be found) before laser scanning for surface displacement measurement. The range data being kept in a computer memory, it then possible to have the range for each measuring location and from the range variation to determine the velocity along the line-of-sight.

Frequency shifting on the other hand is conveniently performed by cascading two acousto-optic frequency shifters. The first element up-shifts the optical frequency by a constant value f (for instance f=40 MHz), whereas the second element down-shifts it by f-$\Delta v$, where $\Delta v$ is proportional to the measured velocity. The second element is driven by a voltage-controlled oscillator, which takes its control signal from the velocity measuring system. When the velocity is zero the given shift is also zero. The first and second elements can be located in the same beam, in which case one shifts up and the other shifts down, or alternatively they can be located on different beams, in which case they both shift in the same direction (either up or down).

Figure 3:
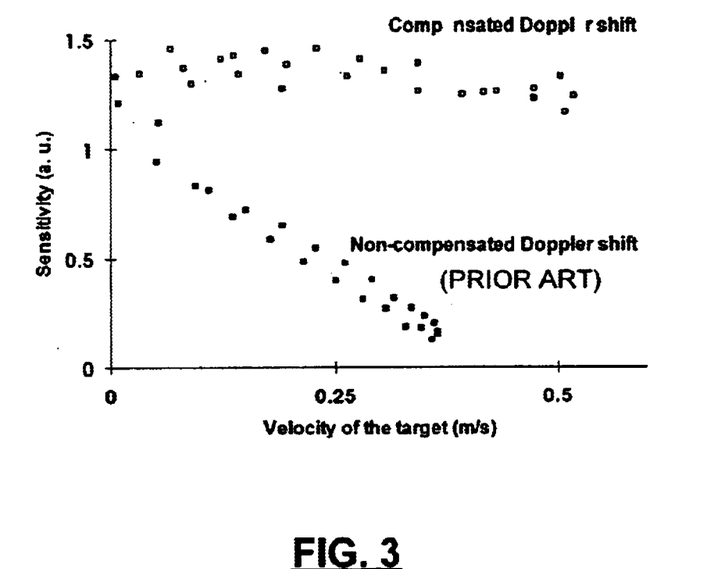
FIG. 3 shows the sensitivity of the TWM-based demodulator with a target having a velocity component in the line-of-sight of the laser with and without compensation system.

It should be noted that when the frequency applied to an acousto-optic cell is varied the output beam also changes direction. In practice the change of frequency is small with respect to the drive frequency and the two-beam adaptive phase demodulator is self-adapting so this effect is of no consequence. Since acousto-optic shifters operate best with small and collimated beams, the frequency compensation scheme is preferably applied on the pumped beam rather than on the signal beam scattered by the object. This beam has a much larger etendue (or throughput) (which means for a given size a much larger divergence). The inventors have tested the principle by sinusoidally shaking an inspected object at a 20 Hz low frequency and by probing the surface during brief windows of 50 $\mu s$ each. During such a brief window the velocity may be considered as constant and known. By sending the information on the velocity to the acousto-optic system, compensation can be made for the Doppler frequency shift induced by the moving target on the signal beam. The results obtained with and without frequency compensation is shown in FIG. 3.

In another aspect the present invention provides an apparatus for probing an object in motion, comprising a laser for generating a laser beam; a beam splitter for splitting said laser beam into a first portion and a second portion, said first portion of said laser beam being directed at said object to generate a signal beam scattered from the surface thereof; a frequency shift determining arrangement for determining the frequency shift produced in the signal beam due to motion of the object; a frequency adjuster for adjusting the frequency of one or both of said first and second portions of said laser beam so that both said second portion of said laser beam and said signal beam have substantially the same frequency; and an arrangement for measuring displacements of said surface by comparing said second portion of said laser beam and said signal beam after said frequency adjustment.

BRIEF DESCRIPTION OF THE DRAWINGS

The invention will now be described in more detail, by way of example only, with reference to the accompanying drawings, in which.

DETAILED DESCRIPTION OF THE PREFERRED EMBODIMENTS

Figure 4:
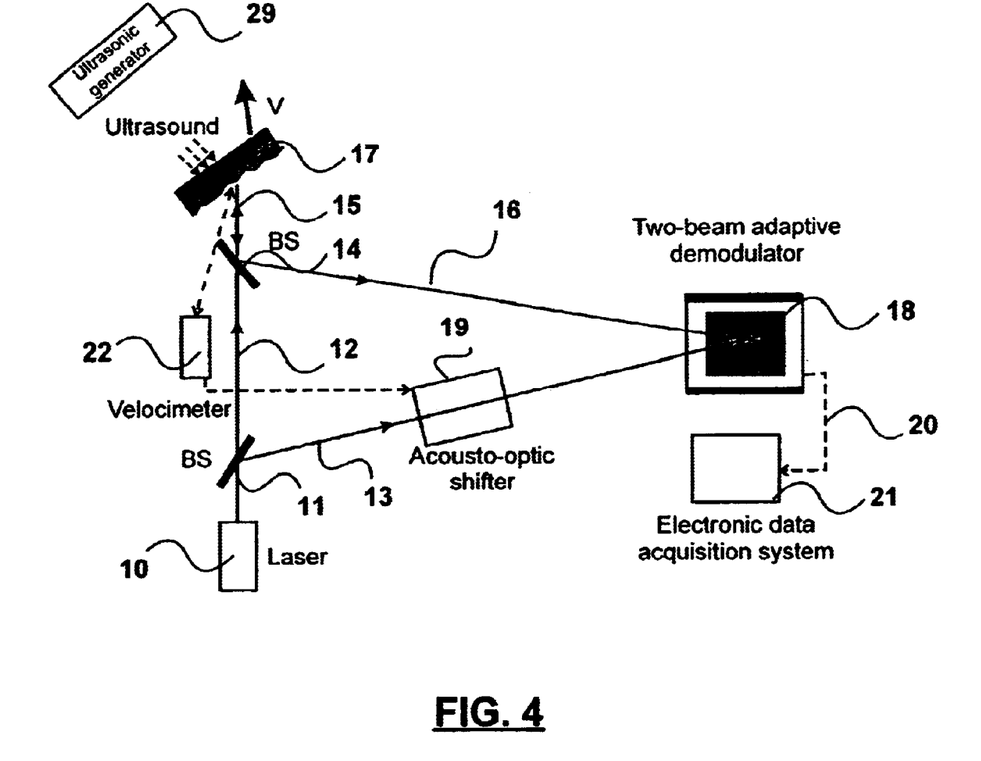
FIG. 4 shows an apparatus in accordance with a first embodiment of the invention.

The apparatus shown in FIG. 4 comprises a laser 10 which outputs a beam that is split in beam splitter 11 into a first portion 12 and a second portion 13 providing a pump beam for the two-beam adaptive phase demodulator 18. The first portion 12 passes through second beam splitter 14 to strike the object 17 energized with ultrasonic energy from an ultrasonic generator 29. The signal beam 15 scattered off the object 17 is then returned to beam splitter 14, which directs it along path 16 to the two-beam adaptive phase demodulator 18. This also receives the second portion or pump beam 13 after it has passed through the acousto-optic phase shifter 19. The demodulator 18 outputs a signal 20, which is passed to an electronic data acquisition system.

Optical Velocimeter 22 generates a signal representing the velocity of the object 17. This signal is fed to the acousto-optic shifter 19.

The adaptive phase demodulator 18 measures the small surface displacements produced by the ultrasonic waves propagating in the object in motion. The optical velocimeter 22 determines the velocity of the object in motion and the acousto-optic frequency shifter 19 tunes the pump beam optical frequency. The velocimeter measurement is fed back to the acousto-optic shifter to compensate for the optical frequency offset between the signal and pump beams produced by the motion of the object. If the velocimeter probing direction is not the same as the displacement probing beam and collection directions, the various angles between these beams should be taken into account in determining the frequency shift produced by the object motion and the required compensation.

Figure 5:
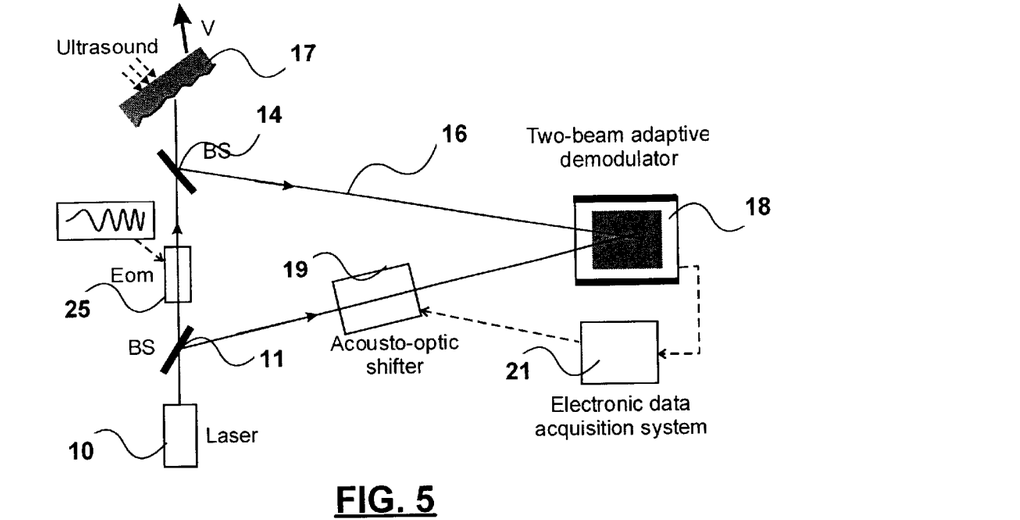
FIG. 5 shows an apparatus for measuring frequency shift with a two-beam adaptive demodulator.

The two-beam adaptive phase demodulator 18 can actually be used to measure both the ultrasonic signal and the frequency shift between the two beams (or velocity). This is shown in the embodiment of FIG. 5. In this embodiment, an electro-optic phase modulator 25, which can be on the signal or on the pump beam, is driven by a frequency chirped signal. To understand the principle of the method, one may first suppose that the two-wave mixing setup shown in FIG. 1 is used, with the modulator driven by a sinusoidal electric voltage at the frequency $vv_m$. When the pump optical frequency is scanned, the detected signal at the modulation frequency presents three maximums for 1) equal optical signal and pump frequencies, 2) for the pump frequency equal to the frequency of one of the sidebands.

Figure 6:
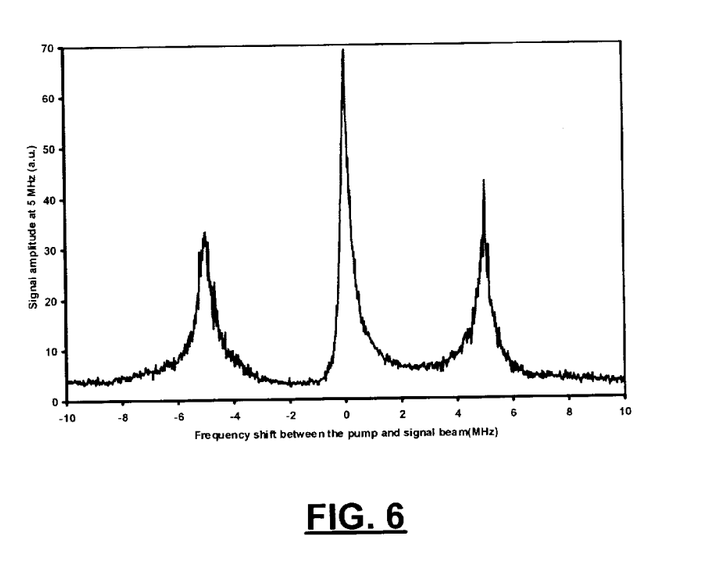
FIG. 6 shows experimental results of the amplitude of the modulated detected signal versus the optical frequency offset of the signal and pump beam with the phase modulator driven at 5 MHz.
Figure 7:
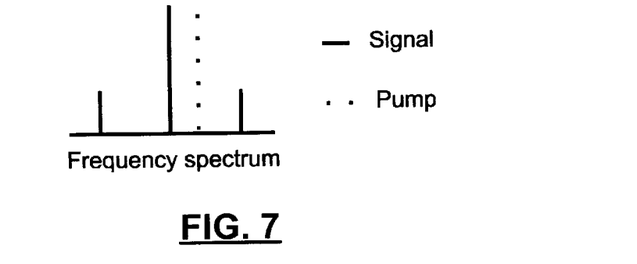
FIG. 7 shows the frequency spectrum of the phase modulated signal beam and of the frequency shifted pump beam.

FIG. 6 gives experimental results of the amplitude of the modulated detected signal versus the optical frequency offset of the signal and pump beam with the phase modulator driven at 5 MHz. The reason for these three peaks is easily understood by looking in the frequency domain. As shown in FIG. 7, the Fourier transform of the phase modulated signal beam is composed of a central peak at the signal optical frequency $v_s$ and two sidebands at $v_s \pm v_m$. The Fourier transform of the pump beam is composed of only one peak at the pump optical frequency. To observe a signal, a space charge field should be written, which means an interference pattern nearly at rest. This condition is fulfilled when the signal and pump optical frequencies are nearly equal, or when the pump frequency nearly equals to one sideband frequency. Since a peak occurs when the pump frequency is nearly equal to one sideband frequency, a velocimeter can be built by scanning the frequency of the phase modulation. This is easily performed by driving the electro-optic modulator with a frequency chirped signal.

Figure 8A:
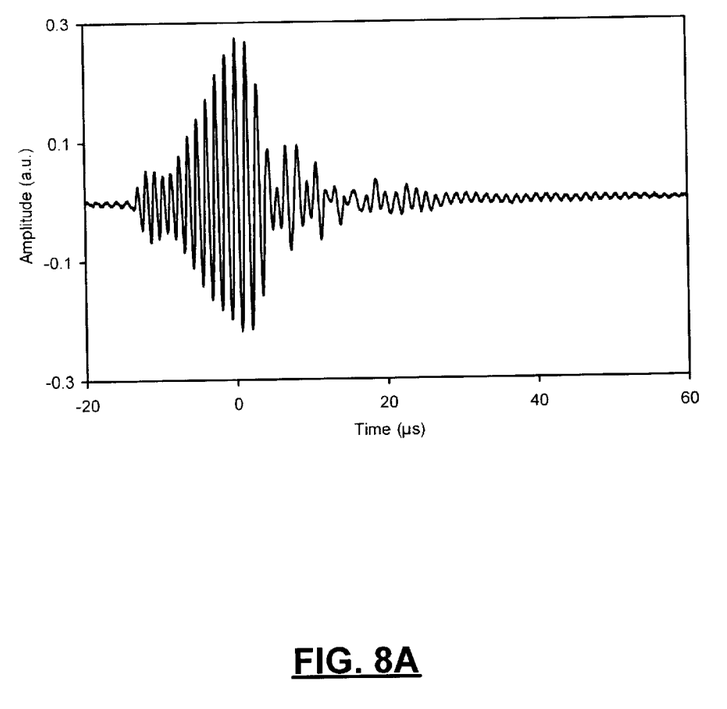
FIGS. 8a and b show the velocimeter signal with a chirped-frequency modulated signal ranging from 1 MHZ to 100 kHz for an optical frequency offset between the signal and pump beam of: a) 750 kHz, b) 250 kHz.
Figure 8B:
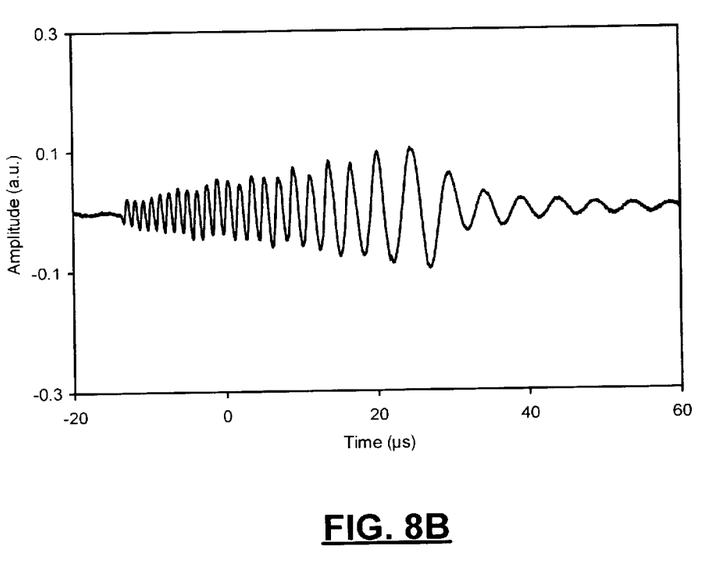
Figure 9:
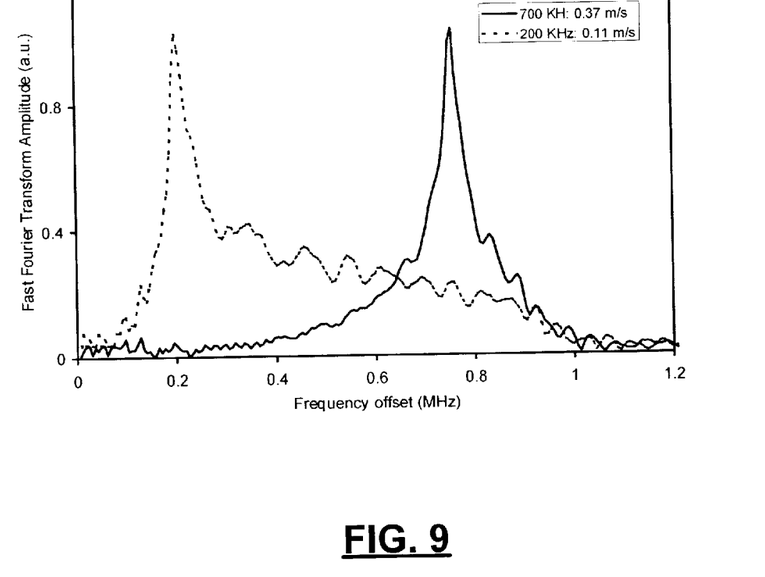
FIG. 9 shows a Fast Fourier Transform of the signals of FIG. 8.

The results are presented in FIG. 8 for a chirp ranging from 100 kHz to 1 MHz, which means a velocity ranging from 0.05 to 0.5 m/s (for a wavelength of about 1 μm). The Fast Fourier Transform of the signal is also presented in FIG. 9. Similar results were obtained with a photo-Emf setup. It should be noted that this method directly measures the frequency shift of the signal instead of the velocity component along the line-of-sight of the incident laser. This frequency shift can then be fed to the acousto-optic shifter. In practice the shift determination and the ultrasonic measurement are done sequentially, for example by using a first part of the detection laser pulse for the shift determination and a second part for the ultrasonic measurement. The ultrasonic generation device (a short pulse laser in laser-ultrasonics) is fired during this second part of this pulse.

Figure 10:
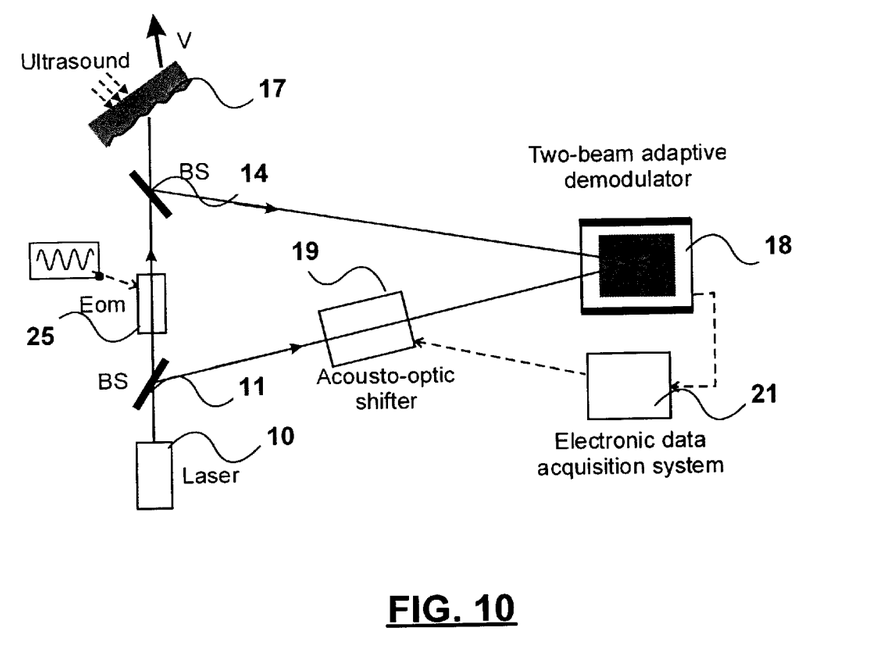
FIG. 10 shows an apparatus that tracks velocity or frequency shifts.

In a further embodiment shown in FIG. 10, which is particularly useful when the velocity of the object is nearly constant and only drifts slowly, the phase modulator 25 on the pump or the signal beam is driven at a frequency outside the range of ultrasonic frequencies of interest for testing the object. The voltage-controlled oscillator (not shown) driving the acousto-optic shifter is ramped and the amplitude of the phase demodulated signal at the driven frequency is monitored. The maximum of signal corresponds to the proper frequency offset. This operation is controlled by a computer and repeated from time-to-time to track any velocity drift.

Figure 11:
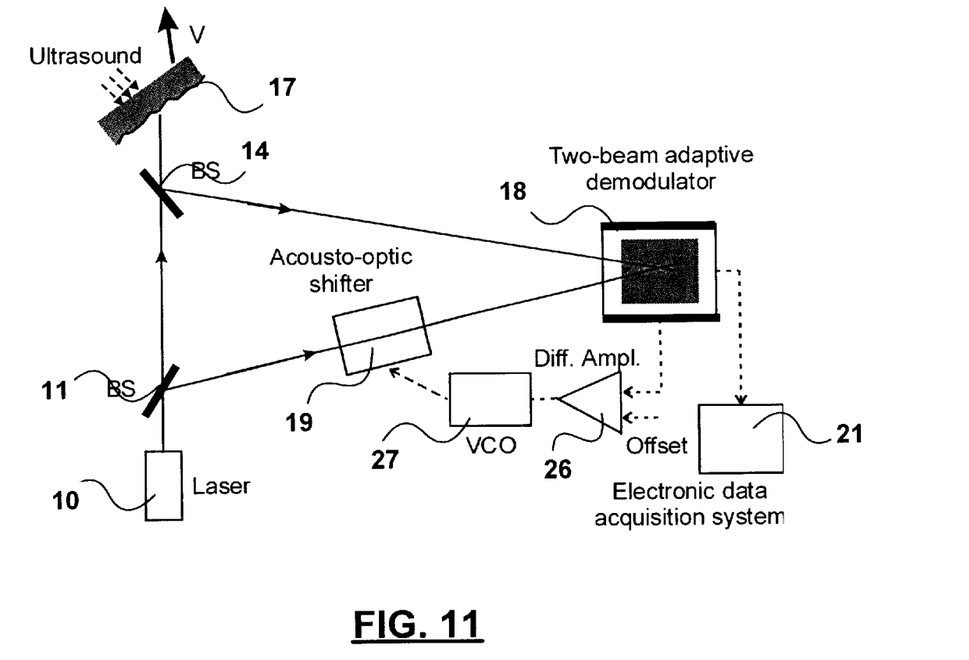
FIG. 11 shows a preferred embodiment of the invention employing continuous frequency tracking and locking.

In the embodiment shown in FIG. 11, the velocity of the object (or the frequency shift) is tracked continuously. In this embodiment, the output from the demodulator 18 is fed back through a differential amplifier 26, with a given offset, and a voltage controlled oscillator 27 to the acousto-optic shifter 19. The principle of this method is the following: when the frequencies of the interfering signal and pump beams are the same, a space-charge grating is created in the two-beam phase adaptive demodulator. If there is no frequency change, the grating is stationary and there is zero signal at output of the demodulator. When there is a change of frequency, a positive or negative signal appears at the output and can be used as an error signal to drive the acousto-optic shifter 19.

The two-beam adaptive demodulator 18 can be of any of the types mentioned above. For the TWM system a balanced receiver (two detectors followed by a differential amplifier) is used at the output of the crystal. It should be noted that it is necessary to find first the proper frequency offset in order to create a stable grating inside the material. Once such a grating is established the feedback loop can be closed and if the loop gain is sufficiently high there is continuous tracking and continuous detection of ultrasonic motion. In practice, one either starts from a situation where there is no frequency shift (e.g. in the case of scanning a contoured part, from a location where the beam is normal to the surface) or as shown in FIG. 11, one gives an offset signal to the acousto-optic shifter. For example this signal could be a ramp and the ramp is stopped as soon as a signal appears at the output of the two-beam adaptive demodulator.

Figure 12:
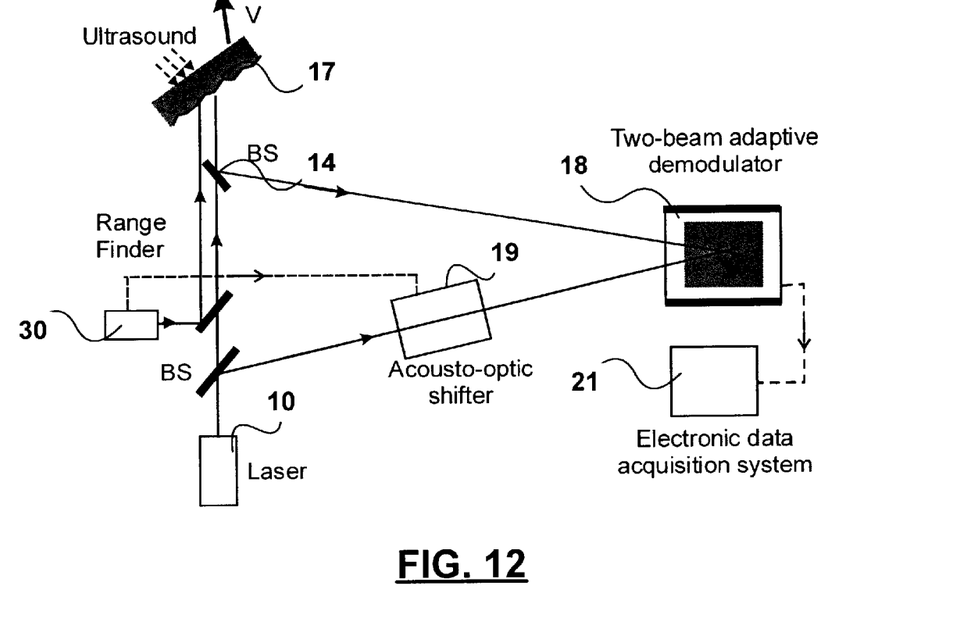
FIG. 12 shows an apparatus that uses a range finder to determine velocity.

Finally, another embodiment, shown in FIG. 12, consists in using a range finder 30 to determine the velocity of the laser spot on the object 17 or of the object itself, as mentioned above. The information on the velocity is then used to drive the acousto-optic shifter to compensate for the Doppler frequency shift.

Although several embodiments of the invention have been described, one skilled in the art will appreciate that many other variations are possible within the scope of the appended claims.

We claim:

1. A method of probing an object in motion, comprising:
   generating a laser beam and splitting said laser beam into a first portion and a second portion;
   directing said first portion of said laser beam at said object to generate a signal beam scattered from a surface thereof;
   determining the frequency shift produced in the signal beam due to motion of the object;
   adjusting the frequency of one or both of said first and second portions of said laser beam so that both said second portion of said laser beam and said signal beam have substantially the same frequency; and
   measuring surface displacements generated by ultrasonic waves propagating in said object by comparing said second portion of said laser beam and said signal beam after said frequency adjustment.

2. A method as claimed 1, wherein said second portion of said laser beam and said signal beam are compared in a two-beam adaptive phase demodulator.

3. A method as claimed in claim 2, wherein the relative velocity of said object is measured, and the frequency shift is determined from said relative velocity.

4. A method as claimed in claim 2, wherein said frequency adjustment is carried out with an acousto-optic frequency shifter.

5. A method as claimed in claim 4, wherein said acousto-optic frequency shifter has a first part that shifts the optical frequency by a constant value in a first direction and a second part that shifts the optical frequency by a value in an opposite direction that is proportional to the measured velocity.

6. A method as claimed in claim 4, wherein said acousto-optic frequency shifter has a first part that shifts the optical frequency by a constant value in a first direction and a second part that shifts the optical frequency by a value in the same direction that is proportional to the measured velocity, one part being located on the first beam portion and the other one on the second beam portion.

7. A method as claimed in claim 3, wherein said velocity is measured by integrating the output of an accelerometer.

8. A method as claimed in claim 3, wherein said velocity is measured with a laser range finder.

9. A method as claimed in claim 3, wherein said velocity is measured with an optical encoder.

10. A method as claimed in claim 3, wherein said velocity is measured using two-beam interferometry.

11. A method as claimed in claim 2, wherein said frequency shift is detected directly from said scattered beam.

12. A method as claimed in claim 11, wherein a phase modulator is placed in said first portion of said beam or said signal beam, and the frequency shift is determined from the frequency of phase modulation of said signal beam.

13. A method as claimed in claim 12, wherein said phase modulator is driven by a chirped signal.

14. A method as claimed in claim 12, wherein said phase modulator is driven at a frequency outside the range of ultrasonic frequencies used to probe said surface.

15. A method as claimed in claim 4, wherein said adaptive demodulator generates an error signal to when there is a change in frequency in said signal beam to control said acousto-optic demodulator to adjust the frequency of one or both of said first and second portions of said laser beam.

16. An apparatus for probing an object in motion, comprising:
    a laser for generating a laser beam;
    a beam splitter for splitting said laser beam into a first portion and a second portion, said first portion of said laser beam being directed at said object to generate a signal beam scattered from the surface thereof;
    a frequency shift determining arrangement for determining the frequency shift produced in the signal beam due to motion of the object;
    a frequency adjuster for adjusting the frequency of one or both of said first and second portions of said laser beam so that both said second portion of said laser beam and said signal beam have substantially the same frequency;
    an ultrasonic generator for generating ultrasonic waves to create displacements of said surface; and
    an arrangement for measuring said displacements of said surface by comparing said second portion of said laser beam and said signal beam after said frequency adjustment.

17. An apparatus as claimed 16, wherein said second portion of said laser beam and said signal beam are compared in a two-beam adaptive phase demodulator.

18. An apparatus as claimed in claim 16, wherein said frequency shift determining arrangement comprises a velocimeter for measuring the relative velocity of said object, said frequency shift being derived from said relative velocity.

19. An apparatus as claimed in claim 16, wherein said frequency adjuster comprises an acousto-optic frequency shifter.

20. An apparatus as claimed in claim 19, wherein said acousto-optic frequency shifter has a first part that shifts the optical frequency by a constant value in a first direction and a second part that shifts the optical frequency by a value in an opposite direction that is proportional to the measured velocity.

21. An apparatus as claimed in claim 19, wherein said acousto-optic frequency shifter has a first part that shifts the optical frequency by a constant value in a first direction and a second part that shifts the optical frequency by a value in the same direction that is proportional to the measured velocity, one part being located on the first beam portion and the other one on the second beam portion.

22. An apparatus as claimed in claim 18, wherein said velocimeter comprises an accelerometer.

23. An apparatus as claimed in claim 18, wherein said velocimeter comprises an optical encoder.

24. An apparatus as claimed in claim 18, wherein said velocimeter comprises an interferometer.

25. An apparatus as claimed in claim 17, wherein a phase modulator is placed in said first portion of said beam, and said two-beam adaptive phase demodulator determines the frequency shift from the frequency of phase modulation of said signal beam.

26. An apparatus as claimed in claim 25, wherein said phase modulator is driven by a chirped signal.

27. An apparatus as claimed in claim 25, wherein said phase modulator is driven at a frequency outside the range of ultrasonic frequencies used to probe said surface.

28. An apparatus as claimed in claim 25, wherein said phase modulator is an electro-optic phase modulator.

29. An apparatus as claimed in claim 17, further comprising a differential amplifier receiving an output of said adaptive phase demodulator responsive to a relative change in frequency of said second beam and said signal beam, and a voltage controlled oscillator driven by an output of said differential amplifier, said voltage controlled oscillator controlling said frequency adjuster.

30. An apparatus as claimed in claim 17, wherein said two beam adaptive demodulator is a two-wave mixing interferometer.

31. An apparatus as claimed in claim 17, wherein said two beam adaptive demodulator is a two-wave mixing interferometer with a balanced receiver.

32. An apparatus as claimed in claim 17, wherein said two beam adaptive demodulator is a photo-Emf based demodulator.

33. An apparatus as claimed in claim 17, wherein said two beam adaptive demodulator is a demodulator based on the polarization self-modulation effect.

* * * * *